(12) United States Patent
Nakajima

(10) Patent No.: US 7,396,346 B2
(45) Date of Patent: Jul. 8, 2008

(54) INDWELLING CATHETER SET

(75) Inventor: Hiroaki Nakajima, Narashino (JP)

(73) Assignee: Medikit Co., Ltd., Bunkyo-ku (JP)

( * ) Notice: Subject to any disclaimer, the term of this patent is extended or adjusted under 35 U.S.C. 154(b) by 682 days.

(21) Appl. No.: 10/602,025

(22) Filed: Jun. 24, 2003

(65) Prior Publication Data

US 2004/0044313 A1    Mar. 4, 2004

(30) Foreign Application Priority Data

Jun. 26, 2002 (JP) ............... P2002-186561

(51) Int. Cl.
*A61M 5/178* (2006.01)
(52) U.S. Cl. ................................. 604/167.03
(58) Field of Classification Search .......... 604/40, 604/110, 263, 158, 162, 177, 256, 264, 900, 604/523, 165.03, 167.01–167.06, 164.01–164.08
See application file for complete search history.

(56) References Cited

U.S. PATENT DOCUMENTS

| | | | | |
|---|---|---|---|---|
| 4,804,372 A | * | 2/1989 | Laico et al. | 604/198 |
| 4,894,055 A | * | 1/1990 | Sudnak | 604/198 |
| 4,897,083 A | * | 1/1990 | Martell | 604/192 |
| 4,929,235 A | * | 5/1990 | Merry et al. | 604/167.04 |
| 5,061,246 A | * | 10/1991 | Anapliotis | 604/171 |
| 5,098,395 A | * | 3/1992 | Fields | 604/168.01 |
| 5,454,790 A | | 10/1995 | Dubrul | |
| 5,562,631 A | * | 10/1996 | Bogert | 604/192 |
| 5,772,636 A | * | 6/1998 | Brimhall et al. | 604/198 |
| 5,911,710 A | * | 6/1999 | Barry et al. | 604/249 |
| 6,083,207 A | * | 7/2000 | Heck | 604/256 |
| 6,120,480 A | * | 9/2000 | Zhang et al. | 604/164.01 |
| 6,814,725 B2 | * | 11/2004 | Gutierrez | 604/508 |
| 2004/0049157 A1 | * | 3/2004 | Plishka et al. | 604/164.09 |
| 2004/0087913 A1 | * | 5/2004 | Rogers et al. | 604/263 |

FOREIGN PATENT DOCUMENTS

| | | |
|---|---|---|
| EP | 0 747 084 A | 12/1996 |
| EP | 0 763 369 A | 3/1997 |
| EP | 1 101 508 A | 5/2001 |
| EP | 1 240 916 A | 9/2002 |
| JP | 3-70502 A | 11/1991 |
| JP | 2001-61971 A | 3/2001 |
| WO | WO 99/26682 A | 6/1999 |

* cited by examiner

*Primary Examiner*—Matthew F Desanto
(74) *Attorney, Agent, or Firm*—Smith Patent Office

(57) ABSTRACT

An indwelling catheter set is provided with a catheter, a cover connected with a proximal end of the catheter and a connector having a hemostatic valve housed therein. The connector is fixed to the cover. A hollow needle for transfusion to a patient is slidably fitted to an inside of the catheter.

4 Claims, 4 Drawing Sheets

INDWELLING CATHETER SET

BACKGROUND OF THE INVENTION

1. Field of the Invention

The present invention relates to an indwelling catheter set for transfusion, which is applied in a case of dialysis treatment, fluid infusion, blood infusion and such, and more particularly, to an indwelling catheter set which effectively prevents blood leakage in every step of the transfusion, for example, inserting the indwelling catheter set to the body of the patient and connecting a blood infusion circuit to the syringe, and which assures safety after drawing out a needle from the body of the patient.

2. Discussion of the Related Art

Japanese Patent Publication of examined application No. H3-70502 discloses a related art of the indwelling catheter set. The application discloses an indwelling catheter set provided with a hemostatic adapter detachably attached to a catheter. The hemostatic adapter is provided with a plurality of packing seals disposed separately with each other, each of which has a cylinder-bottomed shape. When the catheter is drawn out of a needle thereof, the plural packing seals prevent blood leakage.

SUMMARY OF THE INVENTION

When the catheter of the indwelling catheter set of the aforementioned art is connected with, for example, a connector of an infusion circuit of an auxiliary apparatus, the following procedures are necessary. First, the catheter is tied off, second, the hemostatic adapter is uninstalled from the catheter, and finally, the connector is connected with the catheter. There is a problem in that, in the course of the procedures, blood pooled in the catheter tends to leak out, therefore an additional procedure of absorbing the blood by gauze or absorbent cotton is necessary.

The present invention is achieved in view of the above problem.

According to a first aspect of the present invention, an indwelling catheter set is provided with a catheter, a cover fixed to a proximal end of the catheter and a connector with a hemostatic valve housed therein. The connector is fixed to the cover.

According to a second aspect of the present invention, an indwelling catheter set is provided with a catheter, a cramp tube having a first end and a second end, the first end of which is fixed to a proximal end of the catheter, and a connector fixed to the second end.

Preferably, the indwelling catheter set is further provided with an adapter detachably fixed to the connector. The adapter is provided with a second hemostatic valve.

More preferably, the indwelling catheter set is further provided with a hollow needle slidably fitted to an inside of the catheter, a needle cover fixed to a proximal end of the hollow needle and a telescopic pipe having a safety cover. The telescopic pipe is housed in the needle cover so as to be extensible. The needle cover is configured to be connected with the connector. The safety cover covers a distal end of the hollow needle when the telescopic pipe is fully extended.

DETAILED DESCRIPTION OF THE PREFERRED EMBODIMENT

Figure 1:
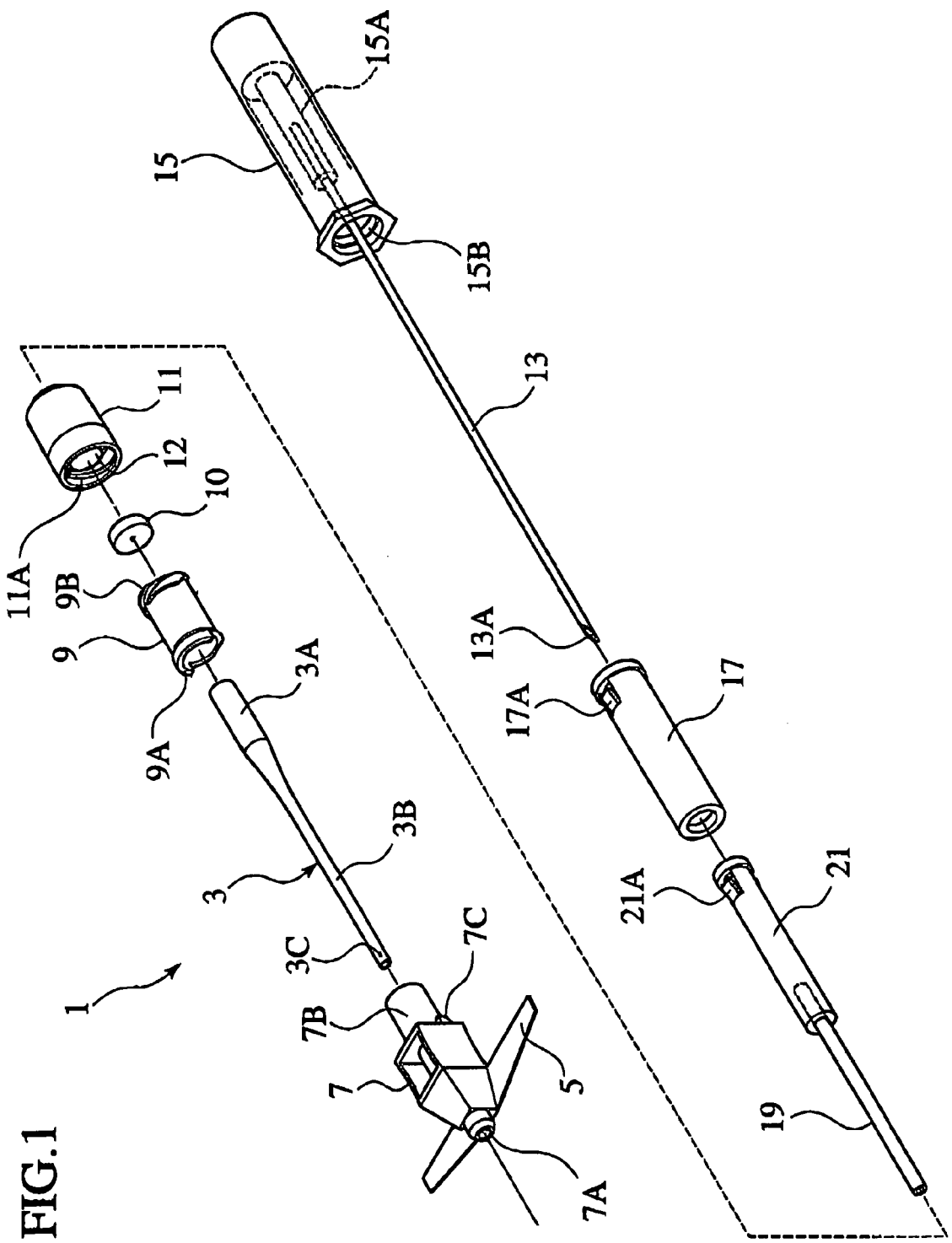
FIG. 1 is an exploded perspective view of an indwelling catheter set according to a first embodiment of the present invention.

A first embodiment of the present invention will be described hereinafter with reference to FIGS. 1-4.

An indwelling catheter set 1 is provided with, similar to a conventional indwelling catheter set, a catheter 3. The catheter 3 is formed in a tube-like shape and is provided with a proximal portion 3A having a larger diameter, a distal portion 3B having a smaller diameter and a tapered portion connecting the proximal portion 3A and the distal portion 3B. The distal portion 3B is formed relatively long and a distal end thereof has a plurality of holes 3C which are penetrated in directions vertical to an axial direction of the catheter 3. The catheter 3 is inserted into an engaging hole 7A of a cover 7 provided with a pair of wings 5 and the proximal portion 3A is tightly fixed to the cover 7 in a state such that the distal portion 3B is projected from the engaging hole 7A.

The cover 7 is provided with a connection portion 7B formed in a tubular shape for fixation of the proximal portion 3A of the catheter 3. The connection portion 7B is provided with a latch portion 7C which is formed in a semicircular shape surrounding a proximal end thereof by half. A distal end of the connector 9 having a tubular shape, to which the connection portion 7B is slidably inserted, is provided with an engaging portion 9A formed in a semicircular shape so as to engage with the latch portion 7C to prevent rotation thereof. The connector 9 houses a hemostatic valve 10 and is further provided with a screw thread portion 9B, also known as an engaging means, on an outer periphery thereof.

The hemostatic valve 10 is made of any elastic materials, such as silicone rubber or natural rubber. The hemostatic valve 10 is formed in a disc shape or a cylinder-bottomed shape and has a valve hole (not shown) in a center thereof so as to allow insertion and extraction of an inner needle 13 and a connector of a blood infusion circuit (not shown). The valve hole is urged to be closed in a steady state and is opened when the inner needle or the connector of the blood infusion circuit is inserted.

A hemostatic adapter 11 having a female screw thread portion 11A in an inner periphery thereof is detachably screwed with the screw thread portion 9B of the connector 9. The hemostatic adapter 11 houses another hemostatic valve 12 constituted of a plurality of packing seals (not shown) which substantially have the same constitution as the related art.

Before use, a tip portion 13A of the inner needle 13 is projected from the distal portion 3A of the catheter 3 and a proximal portion of the inner needle 13 is fixed to a holder 15A having a cylindrical shape which is provided at an axial center of a needle cover 15. A first pipe 17 of a telescopic pipe is movably inserted in the needle cover 15. Furthermore, a second pipe 21 of the telescopic pipe, which has a safety cover 19 formed in a long tube-like shape at a distal end thereof so as to cover the tip portion 13A of the inner needle 13, is movably inserted in the first pipe 17.

Figure 2A:
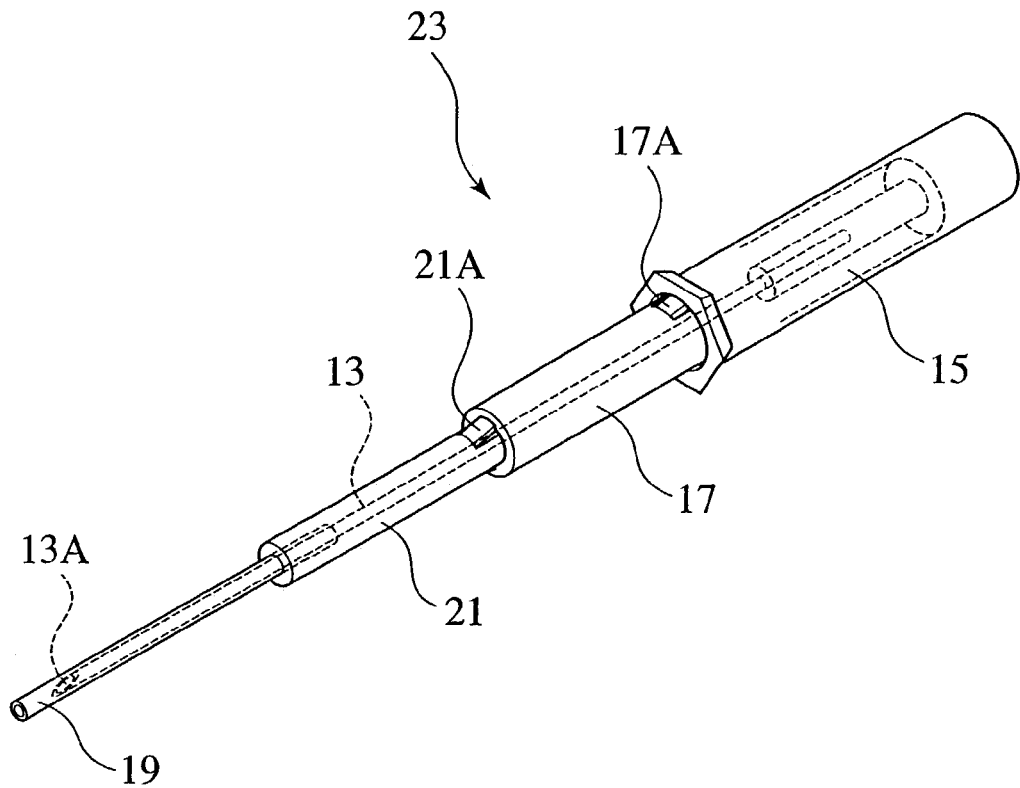
FIG. 2A is a perspective view of a safety cover and an inner needle housed therein according to a first embodiment of the present invention.
Figure 2B:
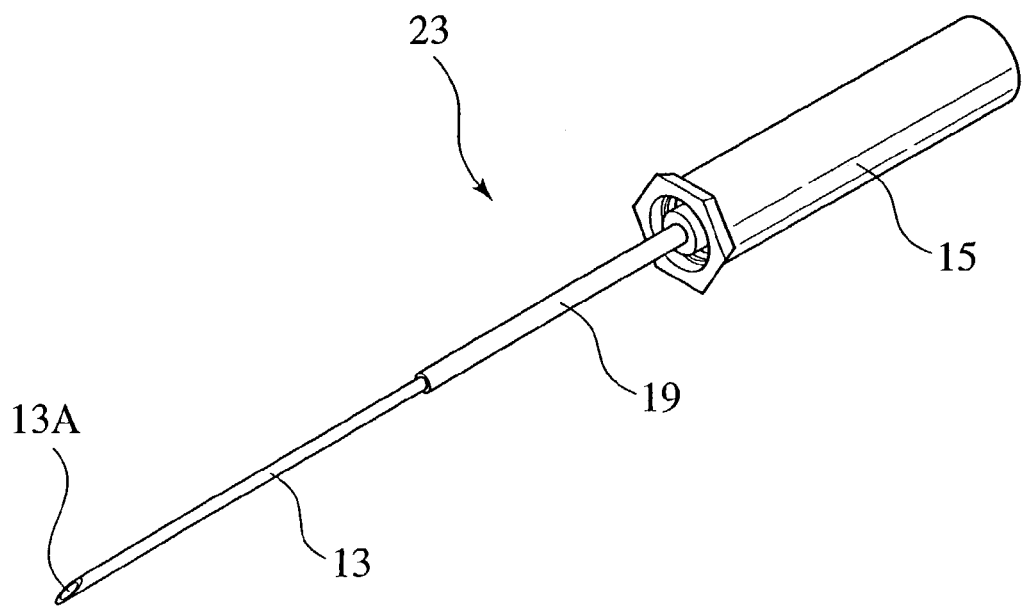
FIG. 2B is a perspective view of the safety cover and the inner needle when the inner needle is exposed.

The telescopic pipe consisting of the first pipe 17 and the second pipe 21 is, before use, housed in needle cover 15 as shown in FIG. 2B and is, after use, projected from the needle cover 15 and extended as shown in FIG. 2A so that the safety cover 19 covers the tip portion 13A of the inner needle 13.

Therefore safety is assured at the time of disposal of the inner needle 13 and such.

Figure 3:
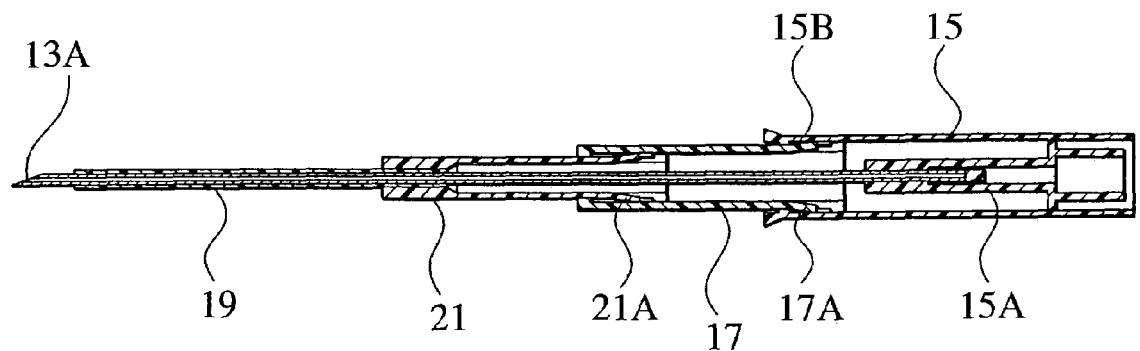
FIG. 3 is a sectional plan view of the safety cover and the inner needle.

A resilient latch 17A is formed on an outer periphery of a proximal end of the first pipe 17 so as to latch with a latch portion 15B formed as a groove on an inner periphery of a distal end of the needle cover 15 as shown in FIG. 3. Thereby a state wherein the tip portion 13A of the inner needle 13 is covered by the safety cover 19 is retained as described above.

In a similar way, a resilient latch 21A is formed on an outer periphery of a proximal end of the second pipe 21 so as to latch with a latch portion (not shown) formed on an inner periphery of a distal end of the first pipe 17.

Therefore it is difficult to draw the telescopic pipe consisting of the first and second pipes 17, 21 into the needle cover 15, once extended.

More specifically, a state wherein the tip portion 13A of the inner needle 3 is covered by the safety cover 19 is retained and safety is assured.

The catheter 3 is inserted into the engaging hole 7A of the cover 7 so that the proximal portion 3A of the catheter 3 is tightly fixed to the engaging hole 7A. Further the hemostatic valve 10 is housed in the connector 9 and the connector 9 is fitted into the connection portion 7B of the cover 7 so as to be fixed. Finally the female screw thread portion 11A of the hemostatic adapter 11 is screwed to the screw thread portion 9B of the connector 9.

Figure 4:
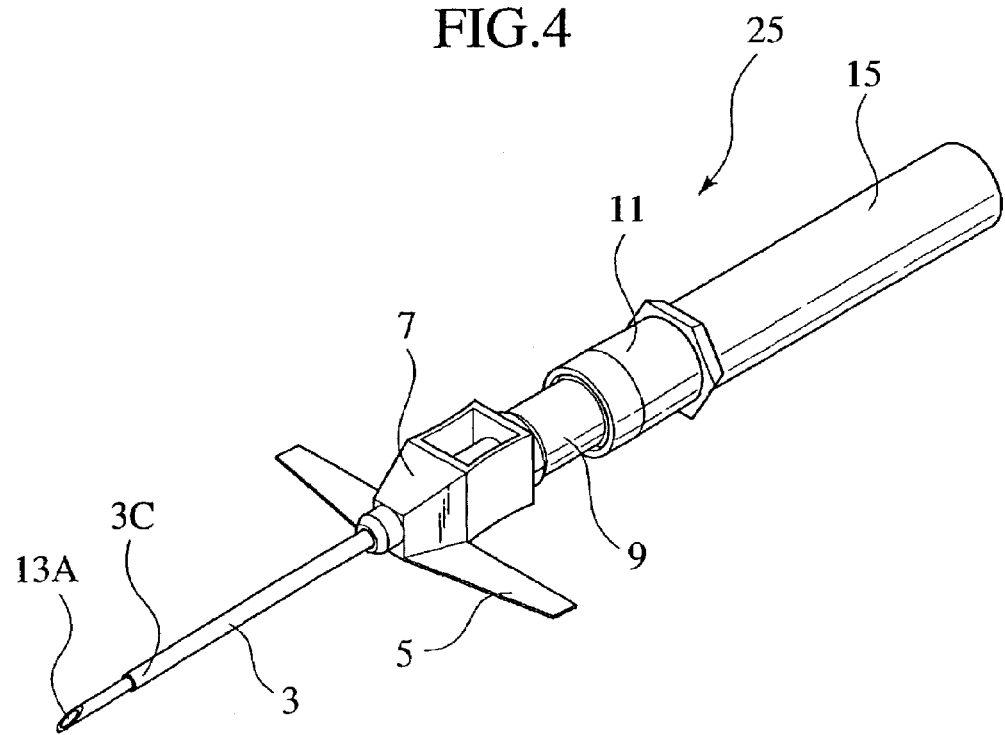
FIG. 4 is a perspective view of the indwelling catheter set in a state before use.

A needle unit 23 is provided with the inner needle 13, the telescopic pipe and the needle cover 15. When the needle unit 23 in a state wherein the telescopic pipe is housed in the needle cover 15 as shown in FIG. 2B is inserted into the hemostatic adapter 11 so that the needle cover 15 abuts the hemostatic adapter 11, the tip portion 13A of the inner needle 13 is slightly projected from a distal end of the catheter 3 as shown in FIG. 4. The state shown in FIG. 4 is a pre-use state of an indwelling catheter set unit 25.

When the indwelling catheter set unit 25 is integrated as described above, a distal end of the safety cover 19 is positioned in the proximal portion 3A of the catheter 3 and a distal end of the second pipe 21 is relatively tightly fitted to an engaging hole (on a blind side of the adapter 11 in FIG. 1) which is formed at a proximal end of the hemostatic adapter 11.

After insertion of the inner needle 13 to a vein of a patient, the needle cover 15 is drawn so that the inner needle 13 is drawn from the catheter 3. Simultaneously the telescopic pipe 17, 21 is extended from the needle cover 15. After the inner needle 13 is perfectly drawn from the catheter 3, the safety cover 19 entirely covers the tip portion 13A of the inner needle 13, thereby assuring safety.

In the course of drawing the inner needle 13, even if in a tilted direction, the inner needle 13 is correctly and smoothly guided by the hemostatic valve 10 and another hemostatic valve of the hemostatic adapter 11 because the hemostatic valves are disposed in a coaxial and separated manner.

Further, in a case where blood is slightly leaked through the hemostatic valve 10 because the inner needle 13 is drawn in a tilted direction, the hemostatic adapter 11 further prevents the leakage. After the inner needle 13 is drawn out, the hemostatic valve 10 is elastically closed so as to prevent leakage.

After the inner needle 13 is drawn out, the hemostatic adapter 11 is uninstalled from the connector 9. When the connector of the auxiliary apparatus, also know as an opposite connector, is inserted and fixed to the catheter 3 through the hemostatic valve 10 or fixed to the connector 9, the hemostatic valve 10 assures air-tightness. Thereby the connector of the auxiliary apparatus can be easily connected with the catheter 3.

As understood from the above description, the connector of the auxiliary apparatus can be easily connected with the catheter 3 without tying the catheter 3 and such treatments according to the present embodiment. Further the inner needle 13 can be safely drawn out of the catheter 3 and the tip portion 13A of the inner needle 13 is automatically covered by the safety cover 19 without treatment with the telescopic pipe 17, 21.

Figure 5:
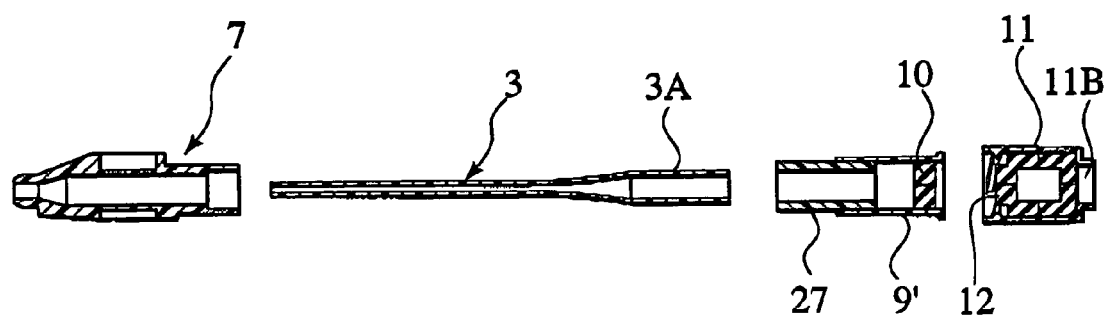
FIG. 5 is a sectional plan view of a catheter, a cover and a connector according to a second embodiment of the present invention.

A second embodiment of the present invention is shown in FIG. 5. In the second embodiment, a tube 27, instead of the connector 9, made of any soft material such as silicone rubber is connected with the proximal portion 3A of the catheter 3 or the cover 7. A connector 9' housing a hemostatic valve 10, similar to the connector 9 of the first embodiment is connected with the tube 27.

The indwelling catheter set of the second embodiment has the same effect as the first embodiment and further, has an effect of prevention of blood leakage by crimping the tube 27. Therefore blood leakage is further prevented.

The contents of Japanese Patent Application No. 2002-186561 (filed Jun. 26, 2002) are incorporated herein by reference in its entirety.

Although the invention has been described above by reference to certain embodiments of the invention, the invention is not limited to the embodiments described above. Modifications and variations of the embodiments described above will occur to those skilled in the art, in light of the above teachings. For example, any changes in shape or design shall be occur unless the changes go beyond the above disclosure.

What is claimed is:

1. An indwelling catheter set for use with an infusion system having an opposite connector, the indwelling catheter set comprising:
    a catheter;
    a cover fixed to a proximal end of the catheter;
    a connector having a hemostatic valve housed in the connector, the connector being fixed to the cover;
    an adapter detachably connected to one end of the connector;
    a hollow needle slidably fitted to an inside of the catheter;
    a needle cover fixed to a proximal end of the hollow needle, the needle cover being configured so as to be connected with the adapter; and
    a telescopic pipe comprising a safety cover, the telescopic pipe being housed in the needle cover so as to be extensible wherein the safety cover covers a distal end of the hollow needle when the telescopic pipe is fully extended,
    wherein the one end of the connector is also connectable with the opposite connector when the adapter is detached so that a flow path for fluid to travel through the infusion system to the catheter is along and parallel with a longitudinal axis of the connector, and
    wherein the adapter includes a second homeostatic valve.

2. The indwelling catheter set of claim 1, wherein the hemostatic valves are disposed in a coaxial and separated manner so as to guide the hollow needle.

3. The indwelling catheter set of claim 1, wherein the hemostatic valve is so disposed in the connector that a portion of the opposite connector is capable to pass through the hemostatic valve when the opposite connector is detachably connected to the one end of the connector.

4. The indwelling catheter set of claim 1, wherein the one end of the connector includes engaging means for making a connection with either of the adapter and the opposite connector.

* * * * *